(12) United States Patent
Alhaqqan

(10) Patent No.: US 10,588,774 B2
(45) Date of Patent: Mar. 17, 2020

(54) URINE COLLECTION DEVICE

(71) Applicant: Ali R. A. A. Alhaqqan, Safat (KW)

(72) Inventor: Ali R. A. A. Alhaqqan, Safat (KW)

( * ) Notice: Subject to any disclaimer, the term of this patent is extended or adjusted under 35 U.S.C. 154(b) by 3 days.

(21) Appl. No.: 16/178,707

(22) Filed: Nov. 2, 2018

(65) Prior Publication Data

US 2019/0159927 A1 May 30, 2019

Related U.S. Application Data

(60) Provisional application No. 62/590,665, filed on Nov. 27, 2017.

(51) Int. Cl.
*A61M 1/00* (2006.01)
*A61F 5/451* (2006.01)
*A61F 5/44* (2006.01)

(52) U.S. Cl.
CPC ............ *A61F 5/451* (2013.01); *A61F 5/4408* (2013.01); *A61F 5/4407* (2013.01)

(58) Field of Classification Search
CPC ....... A61F 5/451; A61F 5/4408; A61F 5/4407
USPC ........................................................ 604/317
See application file for complete search history.

(56) References Cited

U.S. PATENT DOCUMENTS

| 3,194,238 | A | 7/1965 | Breece, Jr. |
| 4,270,539 | A | 6/1981 | Michaud |
| 5,135,199 | A | 8/1992 | Cross et al. |
| 7,658,730 | B2 | 2/2010 | Conley |
| 2011/0270203 | A1* | 11/2011 | Sharpe ................... A61F 5/451 604/326 |
| 2013/0237964 | A1 | 9/2013 | Kicos |
| 2013/0261573 | A1* | 10/2013 | Rackley .................. A61F 5/44 604/328 |
| 2017/0100276 | A1* | 4/2017 | Joh ........................ A61F 5/451 |

FOREIGN PATENT DOCUMENTS

CA 1004104 1/1977

OTHER PUBLICATIONS

"Afex Incontinence Management System" http://www.elderstore.com/-afex-incontinence-management-system.aspx.
"Hollister Urinary Leg Bag Combination Pack" http://www.hollister.com/en/products/Continence-Care-Products/Urine-Collectors/Leg-Bag-Systems/Urinary-Leg-Bag-Combination-Pack.

* cited by examiner

*Primary Examiner* — Andrew J Mensh
(74) *Attorney, Agent, or Firm* — Richard C. Litman; Nath, Goldberg & Meyer

(57) ABSTRACT

A urine collection device can collect urine excreted from the body while protecting the skin from contact with the urine. The urine collection device includes a urine collection container having an upper opening, a lower opening, a reservoir extending between the upper opening and the lower opening, a one-way valve selectively covering the lower opening, a waistband, a plurality of upper connection straps connected to an upper portion of the urine collection container and the waist band, first and second thigh loops, a plurality of lower connection straps, and first and second storage containers. Each lower connection strap is connected to a respective thigh loop and a lower portion of the urine collection container. The bypass unit is connected to the urine collection container and the first and second storage containers.

7 Claims, 6 Drawing Sheets

URINE COLLECTION DEVICE

CROSS-REFERENCE TO RELATED APPLICATION

This application claims the benefit of U.S. Provisional Patent Application Ser. No. 62/590,665, filed Nov. 27, 2017.

1. FIELD OF THE INVENTION

The disclosure of the present patent application relates to an incontinence device, and more particularly to a hygienic garment for managing incontinence for both male and female use.

2. DESCRIPTION OF THE RELATED ART

Urine elimination from the body in an acceptable manner can present a challenge for many people. Incontinence and over-active bladders, for example, result in undesirable urine leaks for some. Certain activities, such as hunting, competitive sports, and cold-weather outdoor sports also make it difficult for many to reach a restroom facility in a timely fashion.

Many resort to wearing urine collection devices to assist in urine elimination. Existing urinary collection devices are typically invasive, complex, and uncomfortable. Invasive devices may place the user at a heightened risk for urinary infections. Disposable diapers, incontinence pads, or undergarments with absorbent features provide alternatives to invasive devices, but generally cause urine to contact the user's skin, are cumbersome to wear, and/or are not reusable.

Thus, a protective garment for solving the aforementioned problems is desired.

SUMMARY OF THE INVENTION

A urine collection device can collect urine excreted from the body while protecting the skin from contact with the urine. The urine collection device includes a urine collection container having an upper opening, a lower opening, a reservoir extending between the upper opening and the lower opening, a one-way valve selectively covering the lower opening, a waistband, a plurality of upper connection straps connected to a portion of the urine collection container and the waist band, first and second thigh loops, a plurality of lower connection straps, and first and second storage containers. Each lower connection strap is connected to a respective thigh loop and a portion of the urine collection container. The bypass unit is connected to the urine collection container and the first and second storage containers. The bypass unit receives fluid flowing through the one way valve and directs the fluid into at least one of the storage containers.

The urine collection device can be washed and reused. In an embodiment, the urine collection device includes a flushing tube through which a cleaning fluid may be directed into the device while the device is worn by a user.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
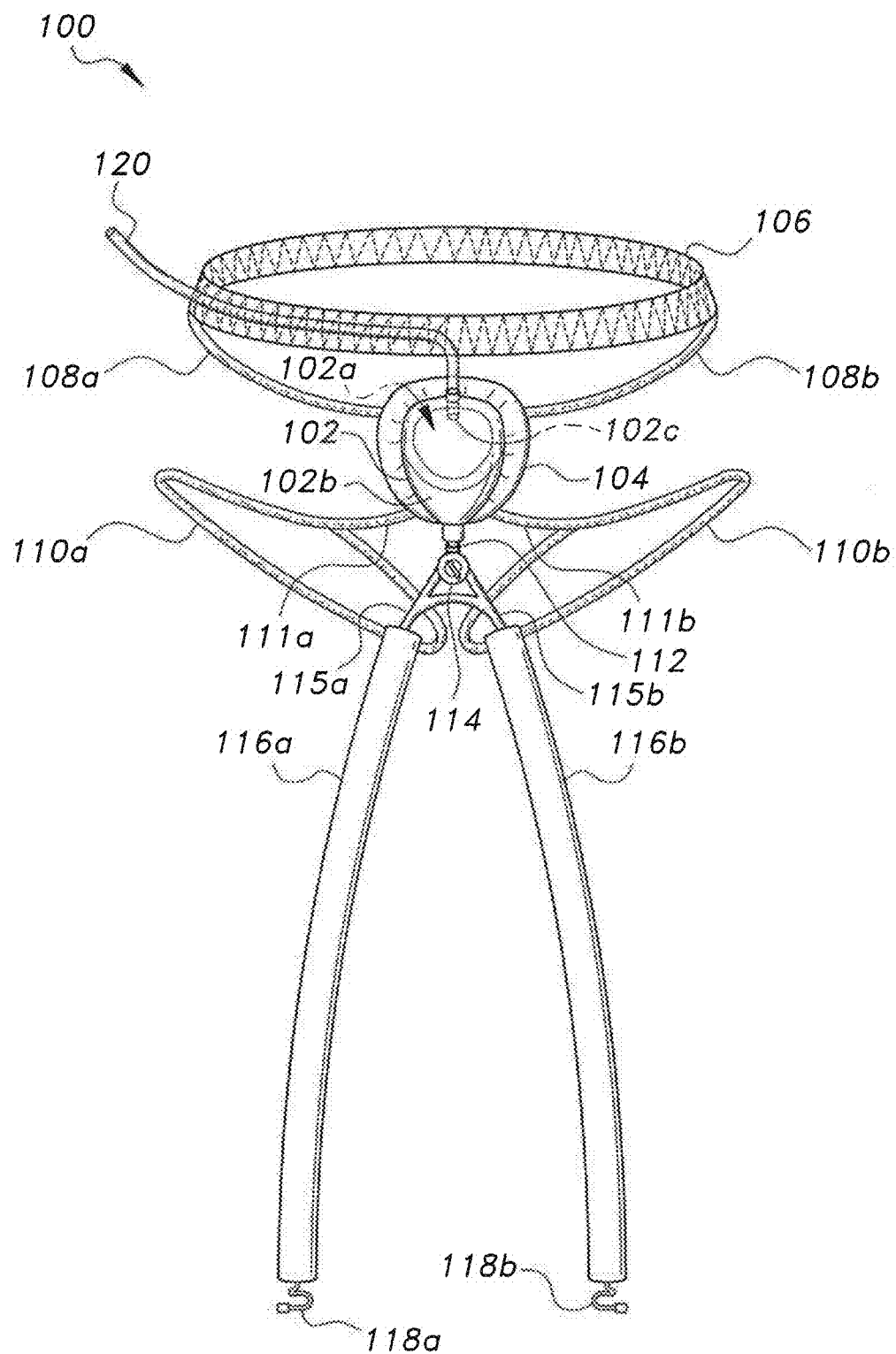
FIG. 1 is a perspective view of a urine collection device according to the present teachings.
Figure 2:
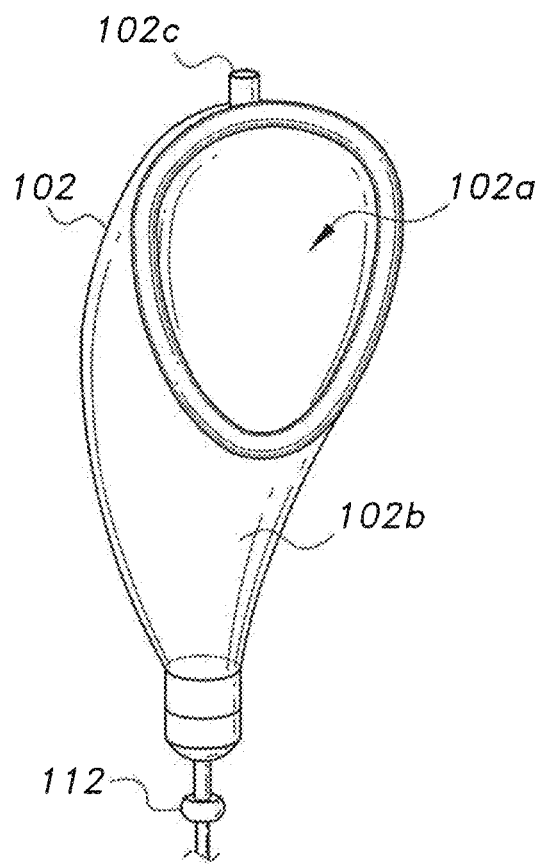
FIG. 2 is a perspective view of the urine collection container according to the present teachings.
Figure 3A:
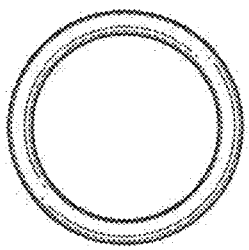
FIG. 3a is a plan view of an embodiment of the urine collection container having a circular opening (for males).
Figure 3B:
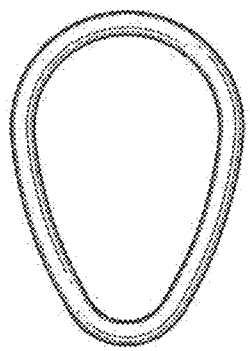
FIG. 3b is a plan view of an embodiment of the urine collection container having a triangular opening (for penile atrophy).
Figure 3C:
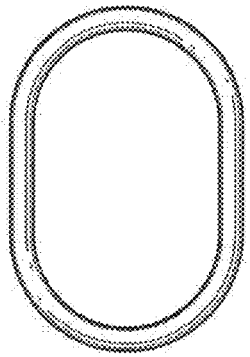
FIG. 3c is a plan view of an embodiment of the urine collection container having an oval opening (for women).

A urine collection device 100 includes a urine collection container 102 that corresponds to a user's crotch region when worn and collects urine excreted from the body. As shown more clearly in FIG. 2, the urine collection container 102 includes an opening 102a in an upper portion through which urine may flow into the container 102 and a reservoir 102b in a lower portion, below the opening 102a, that can collect the urine. The opening 102a can have a generally circular, triangular, or oval shape, as shown in FIGS. 3a, 3b, and 3c, respectively. A rim of the opening 102a has an outward extending flange 104 which can abut the area surrounding the wearer's genitals and protect the user's skin. The reservoir 102b of the urine collection container 102 can have a tapering diameter to prevent unwanted interaction with the thighs during movement.

A waistband 106 is connected to the urine collection container 102 by two upper straps 108a, 108b. Non-limiting examples of the waistband 106 include an elastic waistband and a waistband having a belt configuration. Preferably, each upper strap 108a,b extends from the waistband 106 to an upper portion of the flange 104 of the urine collection container 102. The urine collection container 102 is connected to thigh loops 110a,b by lower straps 111a,b. Preferably, each thigh loop 110a,b is connected to a lower portion of the flange 104 by the respective lower straps 111a,b. The flange 104 may be made out of a material that prevents user discomfort, e.g., foam, rubber, or any suitable textile. Alternatively, a pad may be placed around the rim of the opening 102a.

The thigh loops 110a,b, upper straps 108a,b, lower straps 111a,b, and waistband 106 secure the device 100 to the user and may be adjustable to accommodate the dimensions of the user's body or an activity to be performed by the user. For example, a user that intends to play a sport or engage in other intense physical activity may prefer the device to be secured tighter than would be required otherwise. While adjustable elastic bands may be used, any suitable adjustable belt may be used for the thigh loops 110a,b, upper straps 108a,b, lower straps 111a,b, and waistband 106.

Figure 4:
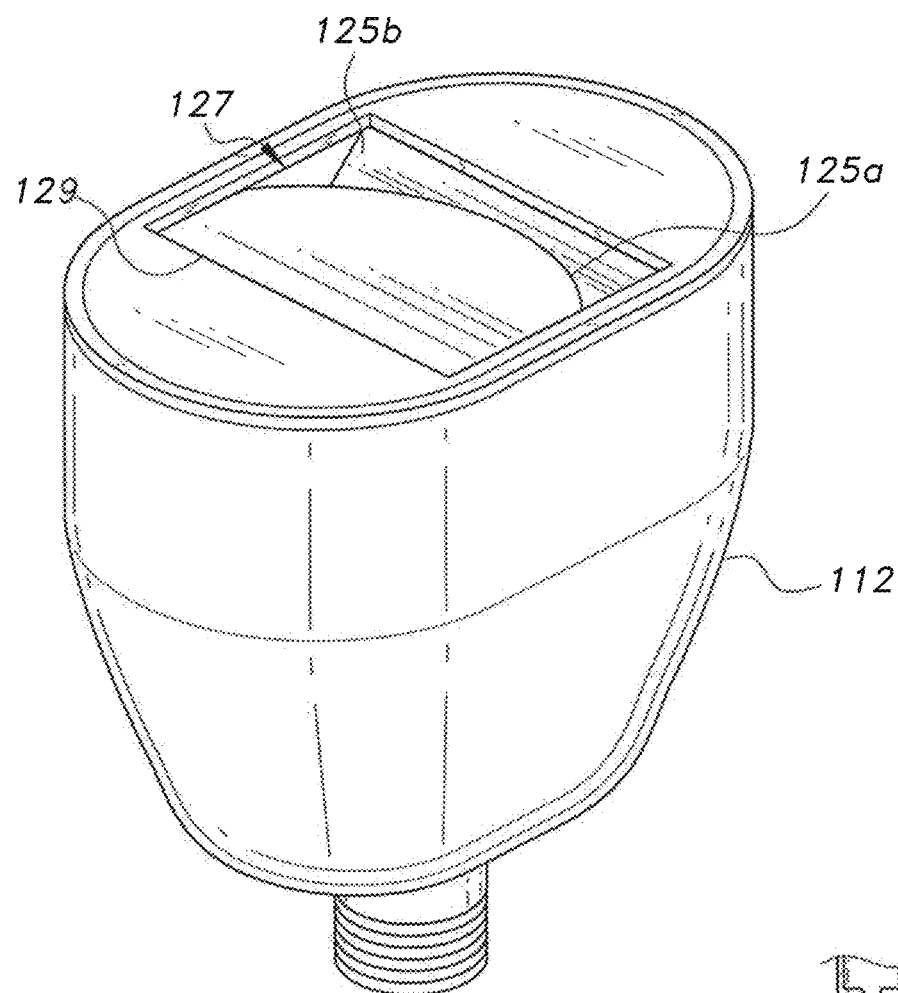
FIG. 4 is a perspective view of the one-way valve.

As shown more clearly in FIG. 4, a bottom of the reservoir 102b includes a one way valve 112 that allows fluid received in the reservoir 102b to exit the urine collection container 102 and pass to storage containers 116a,b. Once urine passes out of the collection container 102 through the valve 112, the valve 112 prevents the urine from flowing back into the collection container 102.

The storage containers 116a,b can have any suitable configuration and shape, e.g., cylindrical with an elliptical or circular cross-section. User releasable valves 118a, b, respectively, can be provided at a bottom of each storage container. The valves 118a,b allow a user to drain the stored urine when desired. For example, the storage containers can be drained into a toilet or drain. The storage container may be formed from a flexible material that become flat when empty, or a rigid material that retains its shape when empty, such as silicone.

Figure 5:
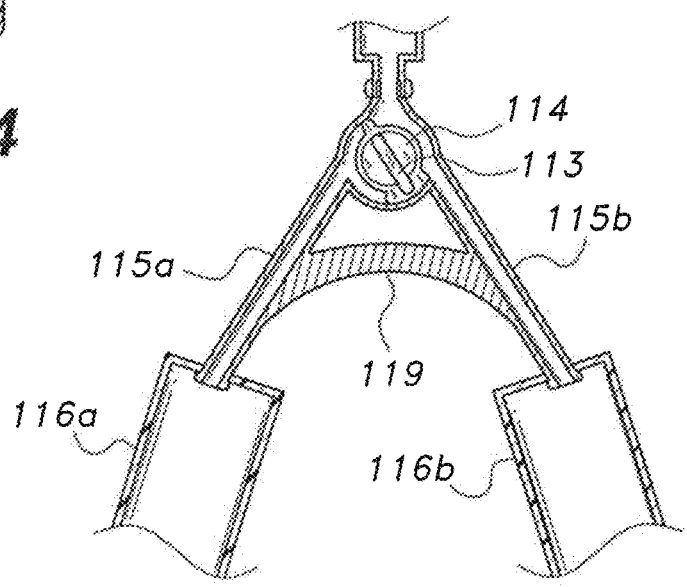
FIG. 5 is an enlarged, perspective view of the bypass unit.

A bypass unit 114 extends between the one-way valve 112 and the storage containers 116a, b (FIG. 5). Urine passing through the one-way valve 112 can pass through the bypass unit 114 prior to reaching the storage containers 116a,b. The bypass unit 114 divides the urine flow into separate streams. The bypass unit 114 can include two transport tubes 115a,b which extend to a respective storage container 116a, b for directing separate streams of urine to the respective storage containers 116a,b.

The waistband 106 can be configured to receive a flushing tube 120 therethrough. The flushing tube 120 can extend through the waistband to a port 102c on a surface of the reservoir to deliver flushing fluid into the urine collection container 102 to clean out the urine collection container 102, the one way valve 112, the bypass unit 114, the storage containers 116a,b, and any intermediate components while the device is on the wearer.

The urine collection container 102 may be made from a suitable flexible or rigid material, such as, silicone, rubber, polyethylene, and latex. In an embodiment, the urine collection container 102 is made from a transparent, bag-like material, as shown in the Figures. Such an embodiment, may be more discrete than more rigid structures.

As shown in FIG. 4, the valve can include two spring loaded flaps 125a,b on opposing sides of the valve opening 127. The flaps 125a,b can rotate downward, but are prevented from rotating upwards beyond the opening 102a by valve rim 129. Springs bias the flaps 125a,b upwards towards the valve rim 129 to seal the valve 112 when no force is applied to the top of the flaps 125a,b. The spring bias can be at a level that allows the flaps 125a,b to open under the weight of urine and remain closed when little or no force is exerted thereon. Accordingly, urine expelled from a user can push the flaps 125a,b open. When urine flows up from the storage containers 116a,b towards the valve, the rim 129 can prevent the flaps 125a, b, from opening. A gasket may be provided at the edge of the flaps 129a,b or the rim 129 of the valve opening 127 to assist in sealing the valve 112.

FIG. 5 shows an embodiment of the bypass unit 114. The bypass unit 114 can include a dial 113 that can be manually operated to open or close inlets to the two transport tubes 115a or 115b, and thereby, direct urine to one or both storage containers 116a or 116b for even filling. The bypass unit 114 can include a horizontal tube 119 that extends between the transport tubes 115a,b. The tube 119 can allow the urine to flow freely between the storage containers 116a,b when one storage container becomes full. Therefore, if one storage container fills up before the other, the urine can flow out of the full container to the less full container through the tube 119.

Figure 6:
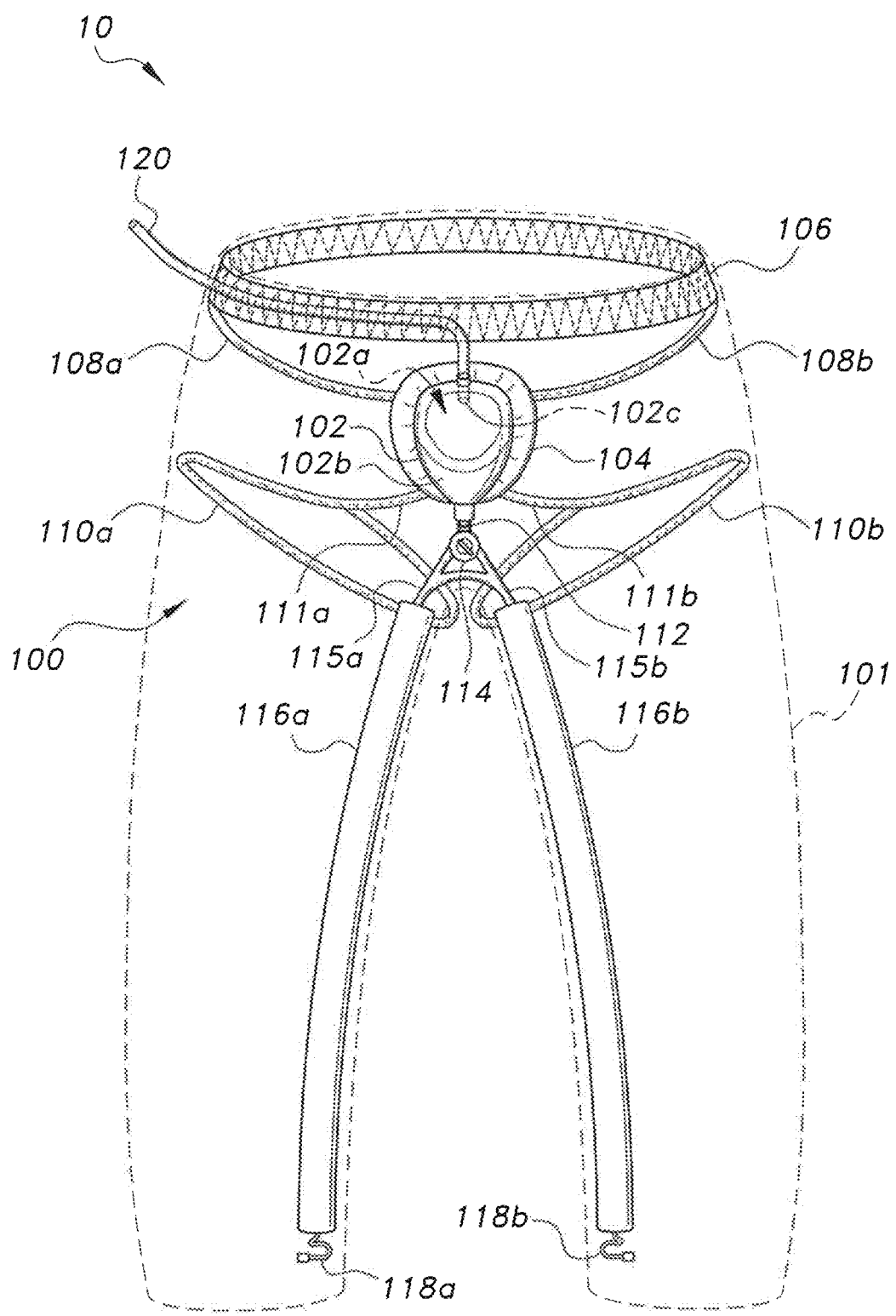
FIG. 6 is a perspective view of a protective garment for incontinence depicted as pants.
Figure 7:
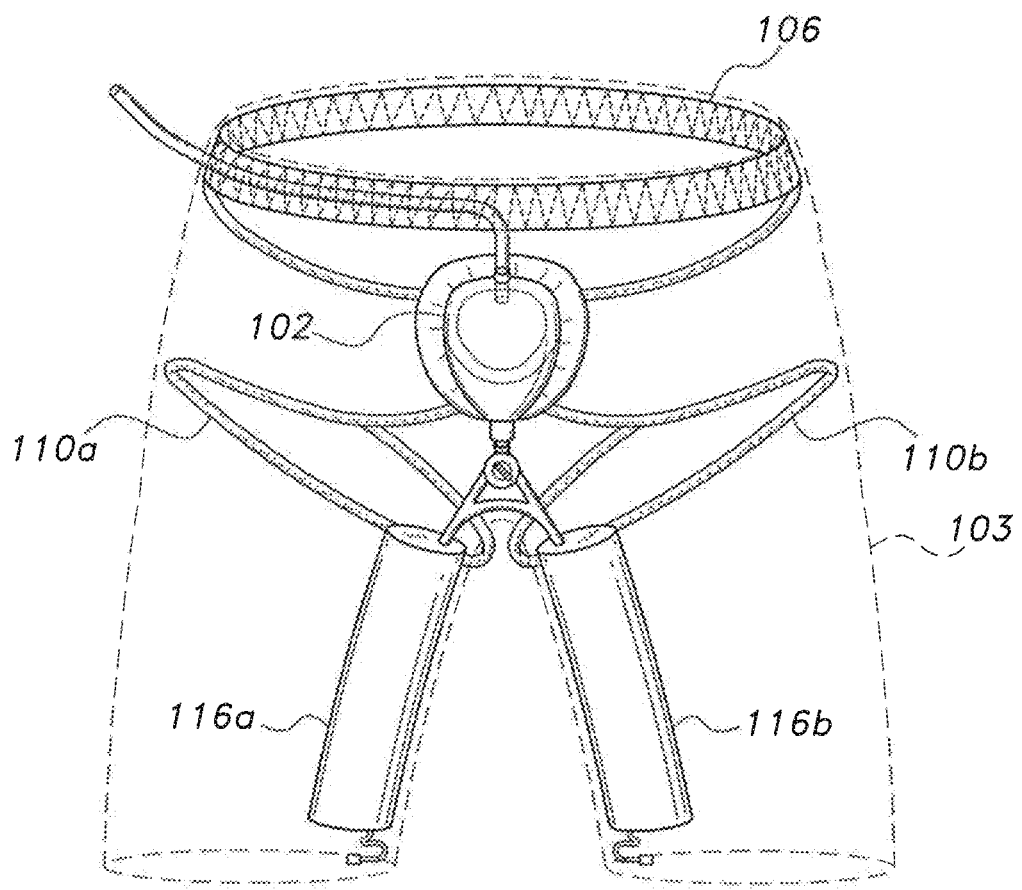
FIG. 7 is a perspective view of a protective garment for incontinence depicted as shorts.
Figure 8:
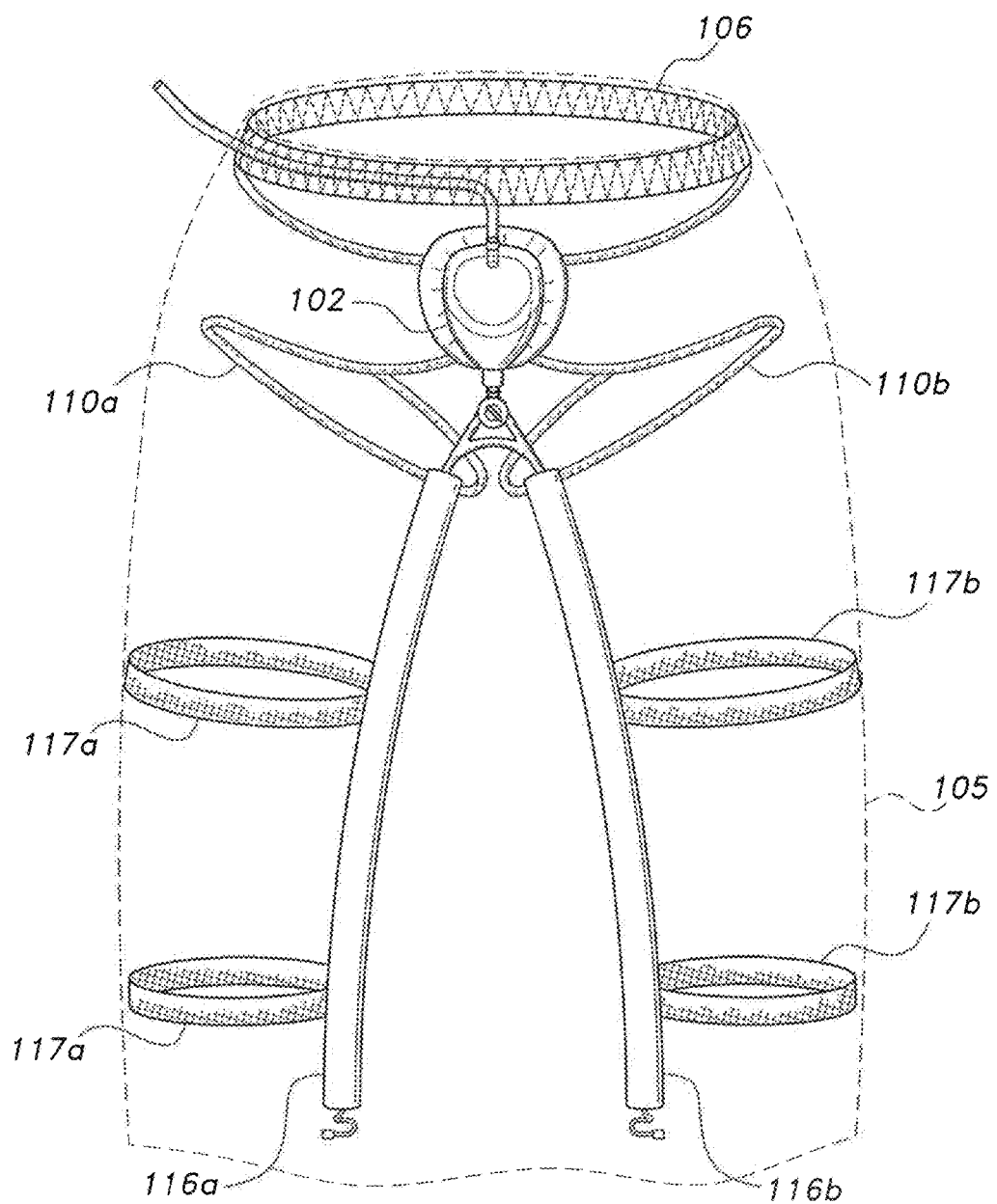
FIG. 8 is a perspective view of a protective garment for incontinence depicted as a dress.

A protective garment 10 for incontinence, shown in FIGS. 6-8, can include a protective outer layer 101 and the urine collection device 100. The protective outer layer 101 can include pants (FIG. 6), shorts (FIG. 7), or any suitable dress (FIG. 8). The waistband 106 of the urine collection device 100 can be secured to a top end of the protective outer layer 101 to thereby define a single waistband for the protective garment 10. Optionally, the thigh loops 110a,b and/or the storage containers 116a, 116b can be secured to an inner side of the protective outer layer 101, e.g., legs of the pants 101. In an embodiment, the storage containers 116a,b may include supplementary loops 117a,b that can be secured to the wearer's legs. Since many dresses are loosely fitting around the lower part of the body, the urine collection device 100 may benefit from being connected directly to the legs of the wearer. For example, as seen in FIG. 8, the waistband 106 of the urine collection device 100 can be integrated with the waistband of the dress 105 and the thigh loops 110a,b can be securely wrapped around the wearer's thighs using the loops 117a,b.

The present subject matter being thus described, it will be apparent that the same may be modified or varied in many ways. Such modifications and variations are not to be regarded as a departure from the spirit and scope of the present subject matter, and all such modifications and variations are intended to be included within the scope of the following claims.

I claim:

1. A urine collection device, comprising:
   a urine collection container having an upper opening, a lower opening, and a reservoir extending between the upper opening and the lower opening, wherein the collection container has an outer surface, the outer surface having a port formed therethrough;
   a flange extending around the upper opening;
   a waistband;
   a plurality of upper connection straps connected to an upper portion of the urine collection container and the waist band;
   first and second thigh loops;
   a plurality of lower connection straps, each lower connection strap connected to a respective thigh loop and a lower portion of the urine collection container;
   a one-way valve selectively covering the lower opening of the urine collection container;
   first and second storage containers, wherein each of the storage containers have a releasable valve at a lower end thereof;
   a flushing tube extending through the waistband and removably secured to the port on an outer surface of the urine collection container; and
   a bypass unit connected to the urine collection container and the first and second storage containers, the bypass unit includes a control valve, first and second transport tubes, and a tube extending horizontally between the first and second transport tubes and beneath the control valve, each transport tube extending from the bypass unit to a respective first and second storage container, wherein the bypass unit receives fluid flowing through the one way valve and the control valve selectively directs the fluid into a selected one of the first and second transport tubes, further wherein the horizontal tube is configured to allow urine to flow freely between first and second storage containers when one of the storage containers becomes full.

2. The urine collection device according to claim 1, wherein the storage containers further comprise supplementary loops for securing the storage containers to legs of a user.

3. A protective garment for incontinence, comprising:
   a protective outer layer; and a urine collection device, the urine collection device including:
  a urine collection container having an upper opening, a lower opening, and a reservoir extending between the upper opening and the lower opening, wherein the collection container has an outer surface, the outer surface having a port formed therethrough;
a flange extending around the upper opening;
a waistband;
a plurality of upper connection straps connected to an upper portion of the urine collection container and the waist band;
a one-way valve selectively covering the lower opening of the urine collection container;
first and second thigh loops;
a plurality of lower connection straps, each lower connection strap connected to a respective thigh loop and a lower portion of the urine collection container;
first and second storage containers, wherein each of the storage containers have a releasable valve at a lower end thereof;
a flushing tube extending through the waistband and removably secured to the port on an outer surface of the urine collection container; and
a bypass unit connected to the urine collection container and the first and second storage containers, the bypass unit includes a control valve, first and second transport tubes, and a tube extending horizontally below the control valve and between the first and second transport tubes, each transport tube extending from the bypass unit to a respective storage container, wherein the bypass unit receives fluid flowing through the one way valve and the control valve selectively directs the fluid into a selected one of the first and second transport tubes, further wherein the horizontal tube is configured to allow urine to flow freely between first and second storage containers when one of the storage containers becomes full.

4. The protective garment for incontinence according to claim 3, wherein the protective outer layer is configured as pants.

5. The protective garment for incontinence according to claim 3, wherein the protective outer layer is configured as shorts.

6. The protective garment for incontinence according to claim 3, wherein the protective outer layer is configured as a dress.

7. The protective garment for incontinence according to claim 3, wherein the storage containers further comprise supplementary loops for securing the storage containers to legs of a user.

* * * * *